United States Patent [19]
Thomas

[11] Patent Number: 5,867,265
[45] Date of Patent: Feb. 2, 1999

[54] APPARATUS AND METHOD FOR SPECTROSCOPIC PRODUCT RECOGNITION AND IDENTIFICATION

[75] Inventor: Gordon Albert Thomas, Princeton, N.J.

[73] Assignee: NCR Corporation, Dayton, Ohio

[21] Appl. No.: 844,671

[22] Filed: Apr. 17, 1997

Related U.S. Application Data

[63] Continuation of Ser. No. 511,987, Aug. 7, 1995, abandoned.
[51] Int. Cl.$^6$ ........................................................ G01J 3/28
[52] U.S. Cl. .................................................................. 356/328
[58] Field of Search ........................... 356/328, 326, 356/430, 428, 446, 240, 416, 419, 402–411; 250/576, 226; 209/587; 364/526; 186/61; 235/383, 462; 702/134–136, 28, 84

[56] References Cited

U.S. PATENT DOCUMENTS

| | | |
|---|---|---|
| 3,747,755 | 7/1973 | Senturia et al. . |
| 4,029,419 | 6/1977 | Schumann, Jr. et al. . |
| 4,365,148 | 12/1982 | Whitney . |
| 4,656,344 | 4/1987 | Mergenthaler et al. . |
| 4,884,696 | 12/1989 | Paleg et al. . |
| 5,008,518 | 4/1991 | Taussig et al. . |
| 5,166,755 | 11/1992 | Gat .......................................... 356/419 |
| 5,258,825 | 11/1993 | Reed et al. ............................. 356/402 |
| 5,479,258 | 12/1995 | Hinnrichs et al. ..................... 356/326 |
| 5,537,211 | 7/1996 | Dial ......................................... 356/402 |
| 5,559,605 | 9/1996 | Reed ....................................... 356/402 |

FOREIGN PATENT DOCUMENTS

| | | |
|---|---|---|
| 0315939 | 5/1989 | European Pat. Off. . |
| 0461861 | 12/1991 | European Pat. Off. . |
| 0467015 | 1/1992 | European Pat. Off. . |
| 0512204 | 11/1992 | European Pat. Off. . |
| 3160344 | 7/1991 | Japan . |

OTHER PUBLICATIONS

Lingli et al, "A New Colour . . . Robotics" Proceedings of the International Conference on Industrial Electronic Control and Instrumentation (IECON) IEEE, vol. 3, No. 3, Oct. 28, 1991.

(List continued on next page.)

*Primary Examiner*—K. P. Hantis
*Attorney, Agent, or Firm*—Crummy, Del Deo, Dolan, Griffinger & Vecchione; Paul W. Martin

[57] ABSTRACT

An optical identification system includes a light source with a broad wavelength spectrum that is directed on an object to be identified. Suitable optical components, such as, one or more collimating lenses gather light that is reflected from the object and direct this light into a spectrometer. The spectrometer disperses the collimated light using a dispersing element, such as one or more gratings, prisms or a combinations of both, onto an array of detectors. The array of detectors may be comprised of a linear diode array or a charge-coupled device (CCD) array which indicates the amount of light at each of a finely-spaced set of wavelengths covering a wide spectral range. The detectors are sensitive over a wavelength region, for example, in the case of silicon detectors from near-infrared plus the visible region, e.g., from 250 nm to 1100 nm. The set of signals from the detectors is read with an analog to digital converter, and transferred to a computer in the form of a spectrum. A set of known spectra determine the reference spectra and the unknown test spectrum is compared with the reference sets. A software program in the computer compares the test spectrum with reference spectra sets utilizing a statistical program. The program takes into account how much the known spectra vary from one another in addition to the average values. A display reads out a list of possible matches in rank order that have a probability of match greater than a predetermined threshold. An operator checks that the first listed item is correct and either accepts the first choice or indicates the correct choice. As an alternative, the system could automatically accept the first choice.

11 Claims, 5 Drawing Sheets

OTHER PUBLICATIONS

Rhodes et al, "Color Recognition . . . Control", ISA, Advances in Instrumentation and Control vol. 46, Part 01, Jan. 1, 1991.

Good Enough, "Fiber Cable . . . Color" Electronic Design, vol. 38, No. 23, Dec. 13, 1990.

Borggaard et al "Optimal Minima Neural Interpretation of Spectra", American Chemical Society, 1992.

Shewfelt, et al.; Postharvest Handling: A Systems Approach; (1993); pp. 227–232; Academic Press, Inc.

L. Bochereau, et al.; "A Method for Prediction by Combining Data Analysis and Neural Networks: Application to Prediction of Apple Quality using near Infra–Red Spectra"; (1992); pp. 207–216; J. Agic. Eng. Res.

APPARATUS AND METHOD FOR SPECTROSCOPIC PRODUCT RECOGNITION AND IDENTIFICATION

This is a continuation of copending application Ser. No. 08/511,987 filed on Aug. 7, 1995, now abandoned.

FIELD OF THE INVENTION

The present invention relates to the field of optical product identification, and more particularly to the use of optical spectroscopy in combination with mathematical classification techniques to identify products and materials.

BACKGROUND OF THE INVENTION

Bar-code readers are used extensively in the retail grocery industry at checkout stations to identify tagged items affixed with bar-code tags. An item is identified by means of its bar-code using a data base stored in a host computer. Typically, a description of the item and its price are printed on a grocery receipt and an ongoing price total is kept as additional items are scanned. The use of bar-code readers has generally been well received by the public, due in part, to the reliability and reduced time spent in the checkout line. However, a reliable system is needed to identify items for which it is undesirable to attach bar-code labels, for example, fresh produce, such as fruits and vegetables.

Optical characterization of fresh produce has been explored to some extent in the prior art. Some general considerations involved in the optical identification of these products are discussed in a number of publications, including for example, "Postharvest Handling: A Systems Approach", by R. L. Shewfelt and S. E. Prussia (Academic Press. New York). An example of a particular application of produce recognition is a study by L. Bochereau et al. (J. Agric. Eng. Res. (1992) Vol. 51, 207–216) showing that near infrared spectra can be used to determine the quality of golden delicious apples, provided that a careful neural-network analysis is performed in the wavelength range from 1,000 to 1,500 nm.

A number of devices are disclosed in the prior art for use in characterizing products using their optical properties. For example, Japanese patent number 03-160344 to Kenichi Yoneda and assigned to Mitsubishi Heavy Industries, Ltd. discloses a device intended to measure the ingredients of fruits. The device shines near-infrared light onto a piece of fruit, and collects the reflected light with an optical fiber. The light is dispersed with a grating and directed into an array of photo detectors. The electronic signal produced is then normalized to a reference signal and the resulting spectrum is then used to characterize the sweetness of the fruit, using the near-infrared region of the spectrum only.

Another device utilizing color-vision in conjunction with measurements of other properties is described in U.S. Pat. No. 4,884,696 to Pelag for an automatic inspection apparatus. The device utilizes-color vision reflectance and adds to it a color-vision transmission spectra. This color-vision, colorimetry or three-color method determines the effective color using light from three narrow spectral regions and is widely used. The device also includes mechanical probes to measure hardness and electrical probes for measuring dc conductivity.

It is our understanding that although the prior art presents a variety of optical identification techniques, users of the above-described methodologies have experienced some difficulty in regard to making reliable identifications of products, as well as dissatisfaction with respect to the time in which it takes to make an identification. Moreover, the cost of implementing such systems on a wide-scale has also proved to be prohibitive.

It is therefore an object of the present invention to provide an optical identification system for recognizing fresh produce and other products, wherein the system makes reliable identifications and is cost efficient. It is further an object of the present invention to provide an optical identification system which is easily integratable with bar code scanners used in the supermarket industry.

SUMMARY OF THE INVENTION

The present invention is an optical identification system intended for use at retail checkout stations. The system provides optical recognition of products that do not readily lend themselves to standard labeling techniques. In one preferred embodiment of the system, a light source with a broad wavelength spectrum is directed on the object to be identified. Suitable optical components, such as, one or more collimating lenses gather the light that is reflected from the object and direct this light into a spectrometer. The spectrometer disperses the collimated light using a dispersing element, such as one or more gratings, prisms or a combinations of both, onto an array of detectors. The array of detectors may be comprised of a linear diode array or a charge-coupled device (CCD) array which indicates the amount of light at each of a finely-spaced set of wavelengths. The detectors are sensitive over as large a wavelength region as feasible, e.g. for Si detectors from the near ultra-violet through the visible to the near infrared, i.e., for wavelengths from 250 nm to 1100 nm.

The optical spectrum is converted by the detectors into an electrical representation of the spectrum, then changed to digital form by an analog-to-digital converter, and transferred to a computer in the form of a digital, electronic spectrum. A set of known spectra for a single product determines a reference set and the unknown (test) spectrum is compared with the reference sets from many products. A software or firmware program in the computer compares the test spectrum with reference sets utilizing a statistical program. The program takes into account how much the known spectra vary from one another within a reference set, in addition to the average values. The program then computes the most likely match and its probability of match, along with the next most likely matches. The match then allows the purchasing process to proceed. For example, a display reads out a list of possible matches in rank order that have a probability of match greater than a predetermined threshold, for example, greater than 70% probability. An operator checks that the first listed item is correct and either accepts the first choice or indicates the correct choice. As an alternative, the system could automatically accept the first choice.

In a preferred embodiment of the invention, the system is set up at a supermarket checkout counter to identify fresh produce, such as fruits and vegetables, that are not readily identifiable with a bar-code label. In the preferred embodiment, the product to be identified would be sitting on a scale and its weight would also be measured during the identification process. In a similar manner to grocery items containing bar-code labels, the name and price of the item would be printed on a grocery receipt using the item identification, the weight and the price per pound which had been previously stored.

BRIEF DESCRIPTION OF THE FIGURES

For a better understanding of the present invention, reference may be had to the following description of exemplary embodiments thereof, considered in conjunction with the accompanying drawings, in which.

DETAILED DESCRIPTION OF THE DRAWINGS

Figure 1:
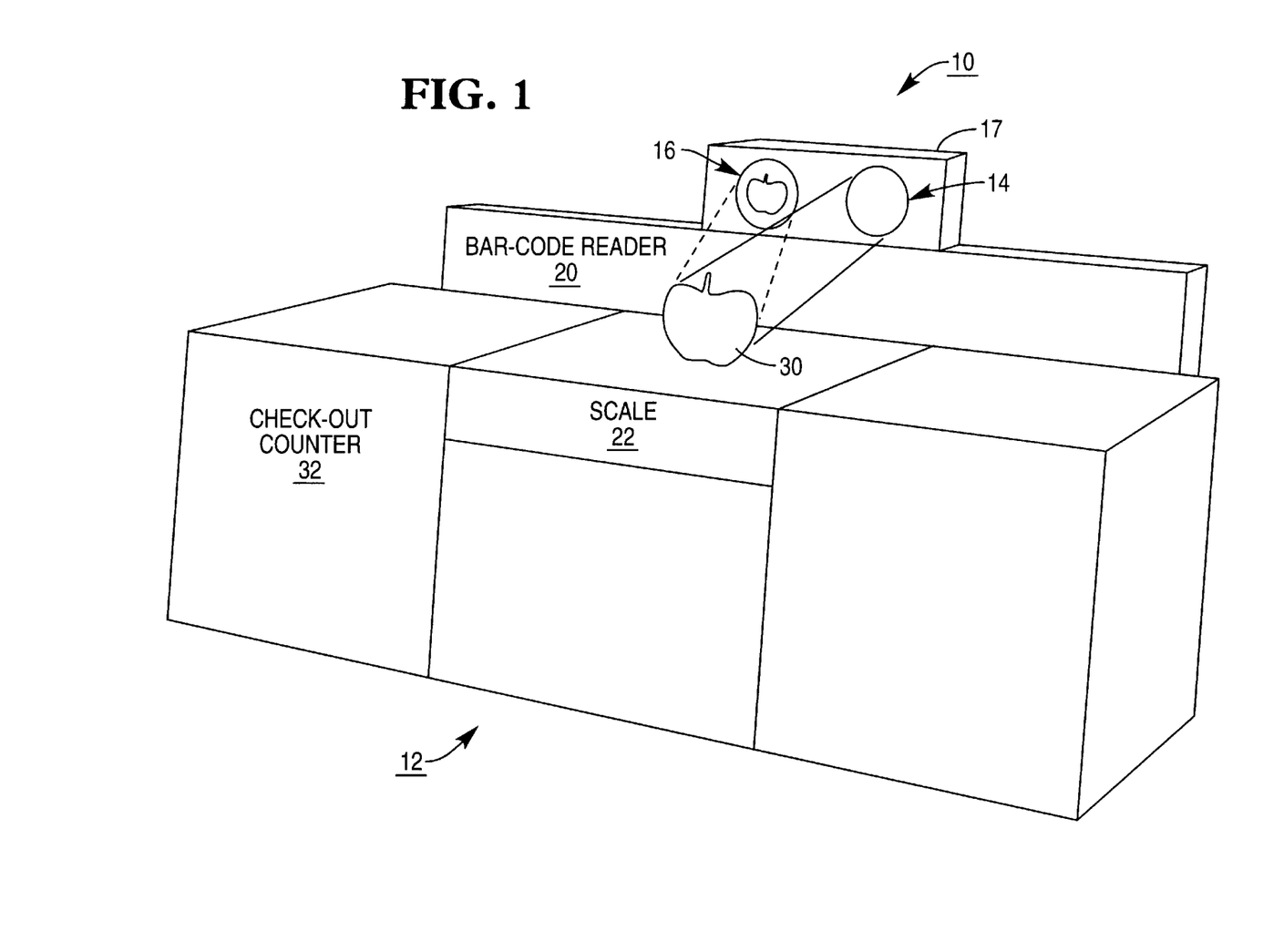
FIG. 1 shows one preferred embodiment of the present invention optical identification system as used in a supermarket checkout.

The present invention is an optical product recognition system which identifies products utilizing spectroscopic methodologies. Referring to FIG. 1, there is shown one preferred embodiment of the present invention product recognition system 10 as it would be utilized in a supermarket checkout station environment. The recognition system 10, as shown, is situated at a checkout station 12 of a supermarket and includes a light source 14 and a light gathering window 16 mounted within a housing 17. The checkout station 12 includes a bar code reader 20 and scale 22, each of which is known in the art, and each of which is electrically coupled to a computing means having operator controls which may, for example, be part of an existing cash register (not shown). The bar-code reader 20 and scale 22 transmit electronic data to the computing means where the data is processed. The recognition system 10 may also be coupled to the computing means, as will be explained. It will also be understood that the computing means need not necessarily be included within the cash register and that the computing means may be a remote device.

As is known, grocery products having bar-coded labels may be scanned at a bar-code reader to identify the product. In most cases, a description of the recognized item and its previously stored price are displayed, printed and automatically tabulated as part of a customer's grocery bill. In the case of grocery items which do not lend themselves to bar-code labeling, such as fresh produce, an alternative methodology is needed to automatically identify an item or items and record the price. As shown in FIG. 1, an item of fresh produce 30 (an apple) is situated on the scale 22 of the checkout counter 32 and is exposed to light having a broad wavelength spectrum which emanates from the light source 14. An example of a suitable light source for producing a broad wavelength spectrum is a tungsten-halogen lamp which produces a useful spectral range including part of the infrared, all of the visible and part of the ultra-violet range.

Figure 2:
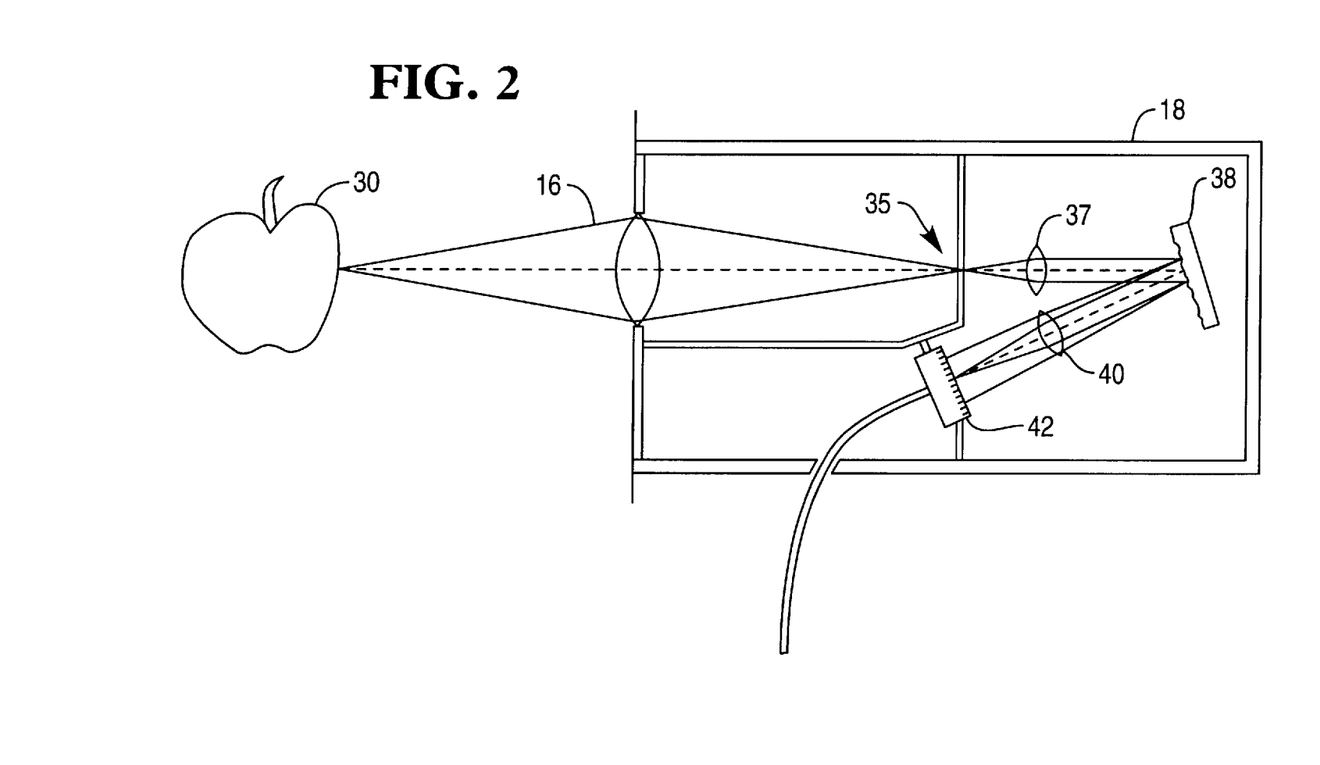
FIG. 2 shows one preferred embodiment of the optical transmission path within a spectrometer of the optical identification system.

Referring to FIG. 2, it can be seen that light is reflected from the produce 30 and received at the light gathering window 16. A suitable optical component which forms the window 16 (comprised, for example, of one or more lenses) gathers the light that is reflected from the produce 30. This light is directed through a slit 35 into a spectrometer 18 contained within the system housing 17. The spectrometer collimates the light with an optical element 37, and disperses the light into a plurality of finely spaced wavelengths using a dispersing element 38, such as one or more gratings, prisms or a combinations of both. It will be understood that a large number of wavelengths are spatially separated by the dispersion of light wherein the number of wavelengths which are resolved may range, for example, between 100 and 1100 individual wavelengths. The dispersed light is transmitted through an optical focusing element 40 onto an array of photo detectors 42. The array of detectors 42 may be comprised, for example, of a linear diode array or a 512×512 element charge-coupled device (CCD) array which indicates the amount of light at each detector. The combination of these elements indicates the amount of light at each of a finely-spaced set of wavelengths. The detectors are chosen to be sensitive over a large wavelength region. For example, Si detectors are useable from the ultra violet to the near-infrared spectra region, i.e. from 250 nm to 1100 nm.

The Si detector devices used with the present invention are well known in the art, and it is intended that off-the-shelf detector components be used, so as to effectively minimize production costs. Other types of detecting elements may also be utilized, for example, photo-diodes made from gallium arsenide and like materials. The spectrometer component 18 of the present invention recognition system 10 utilizes a large number of detectors, typically in a range between 50 and 1100, in order that the light may be recorded at many wavelengths very rapidly and sensitively over a wide range of wavelengths. This is a significant improvement over the prior art in that a wider range of wavelengths allows a more precise identification of the product, and the more finely spaced intervals enable the spectrum to be determined in greater detail. The detector array produces a set of analog signals which are read with suitable electronics such as an analog to digital converter and transferred to a computing means in the form of a spectrum.

Figure 3:
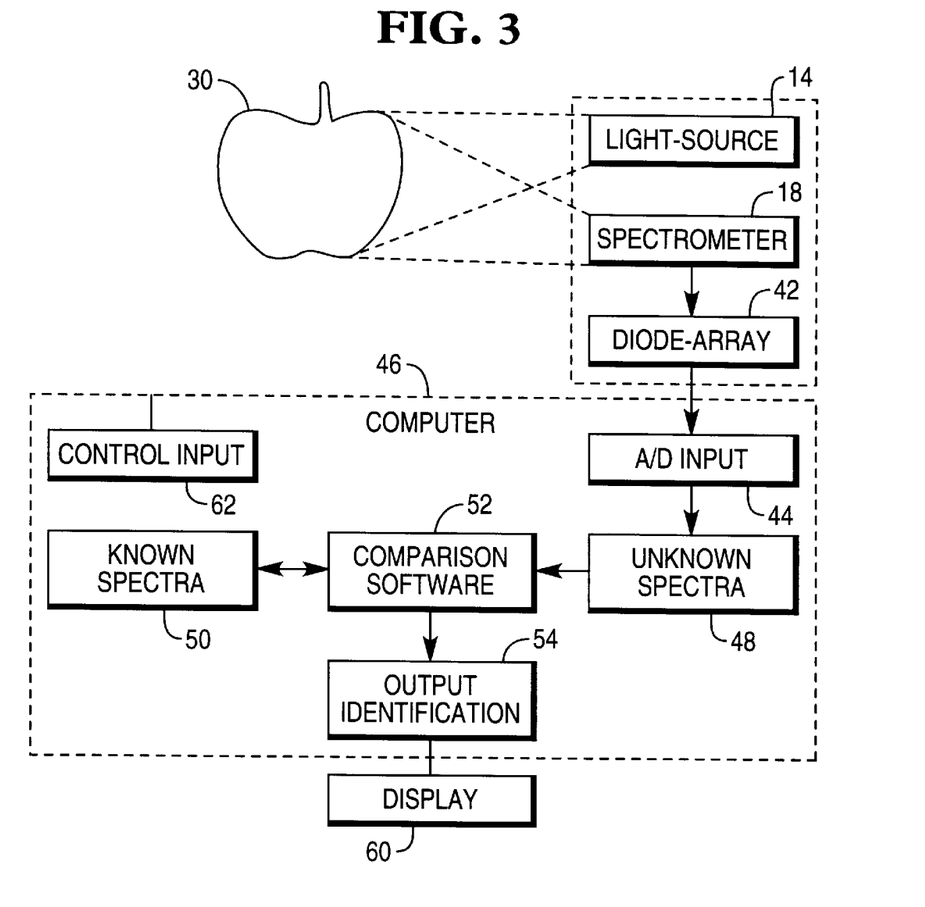
FIG. 3 shows a block diagram for one preferred embodiment of the present invention optical identification system.

FIG. 3 shows a block diagram of the present invention optical illumination and detection system 10 and further illustrates the processing steps which take place within the computing means. As can be seen, the light source 14 outputs a beam of light onto the product to be identified 30 where the light from the source is reflected back and received at the spectrometer 18 which disperses the light into an optical spectrum. As described in FIG. 2, the light from the dispersing element 38 is directed towards an array 42 made up of a large number of detecting elements and which is part of the spectrometer 18. The analog signals from the array are transferred to an analog-to-digital converter 44 and then transferred to the computing means 46 in the form of an electronic representation of the unknown spectrum 48. It will be understood that the A/D converter 44 may be included as part of the computing means 46 as shown in FIG. 3 or as part of a circuit board for handling signals at the diode array 42.

The unknown spectrum 48 sent to the computing means 46 consists essentially of two sets of values, i.e., a first value representing how much signal is produced and a second value representing from what specific detecting device and thus what wavelength produced the signal. A data array of these sets of values is then representative of the spectrum. Sets of known spectra from like identifiable products determine sets of reference spectra 50, and the unknown spectrum 48 is compared with the reference sets 50 using comparison software 52 loaded in the computing means 46. The sets of reference spectra are created from the same type of optical and electronic input to the computer, but from known products. Other software programs perform normalization of all spectra from the reference and unknown products to spectra from a known (flat) white reference substance, wherein the spectra from the reference and unknown products are divided by the white reference spectra to produce the normalized spectra. This is done to produce a more precise comparison of spectra. For the reference set, an operator uses software within the computer to attach an electronic label such as "Macintosh Apple" and a price per unit weight to a set of electronic spectra from the known product. The operator then uses software to group and characterize individual spectra from the known product into a reference set.

The system may also be calibrated by means of software within the computer in order that a specific position of a detector element will correspond to a particular wavelength of light on that element. The calibration is useful for diagnostic purposes in terms of analyzing the spectra and in order to enable consistency of data for systems at different locations. Calibration may be accomplished utilizing a light which produces sharp lines at known wavelength locations, as with an argon gas light. The wavelength scale is then calculated from locations in the array.

Since, as mentioned, more than one grating may used in the spectrometer to disperse light, there may be some overlap in the wavelengths which are dispersed. The software is adapted to account for the overlap and combine the spectra from the different parts (or gratings) of the spectrometer without error. This is able to be accomplished since the specific wavelengths have been calibrated to specific element locations.

Whenever a spectrum is recorded, some sort of indication may be given to the operator, for example, in the form of an audible tone, to indicate that the spectrum 48 has sufficient signal to noise ratio to be used in further data processing. The software or program 52 in the computer 46 compares the test spectrum 48 with reference spectra sets 50 utilizing a statistical program, such as, a matrix least-squares fitting routine. The program 52 takes into account how much the known spectra vary from one another in addition to the average values. In an embodiment of this invention where a CCD array is used as the photo detector. a set of test spectra is obtained from different physical locations on the product, for example, from top to bottom of a piece of fruit, thus including texture. The program then computes the most likely match for the single unknown spectrum or the set of unknown spectra. The program also calculates an indicator of the closeness of the match, such as a probability, along with the next most likely possible matches and their probabilities. As can be seen, the computer may be coupled to a display device 60, which is in turn coupled to an input device 62, such as a touch screen or keyboard for making operator selections. It will be understood that the display and input device may also be part of an existing cash register/checkout system, or alternatively that the system may be automated.

Figure 4A:
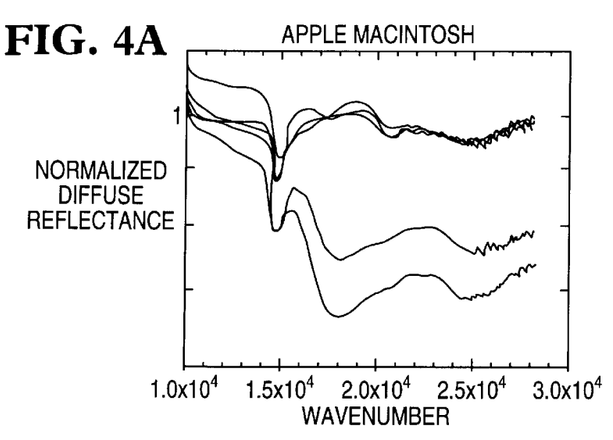
FIG. 4A shows a graph of a set of reference spectra for different locations on a macintosh apple, wherein diffuse reflectance is plotted versus wavenumber, where wavenumber is the inverse of wavelength.
Figure 4B:
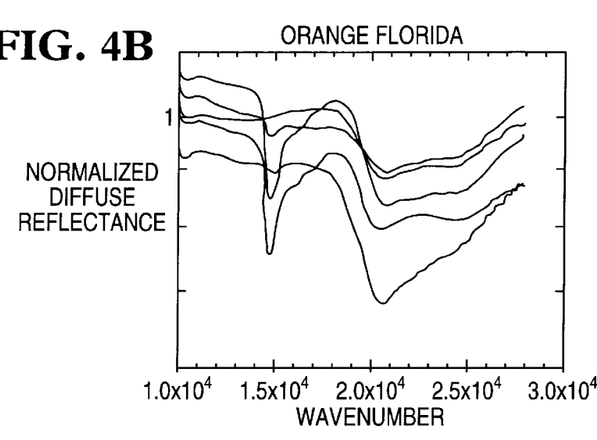
FIG. 4B shows a graph of a set of reference spectra for a Florida orange.
Figure 4C:
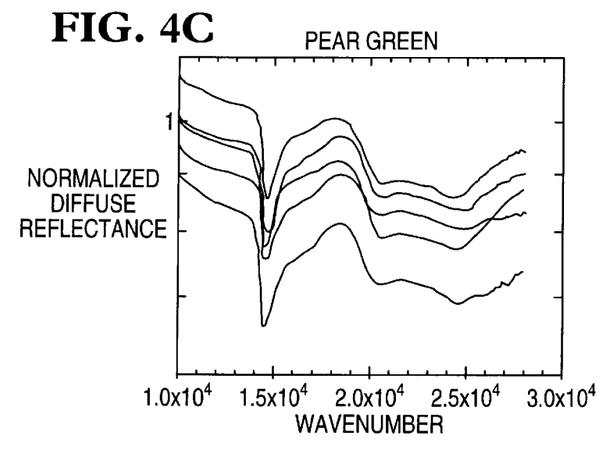
FIG. 4C shows a graph of a set of reference spectra for a green pear.
Figure 4D:
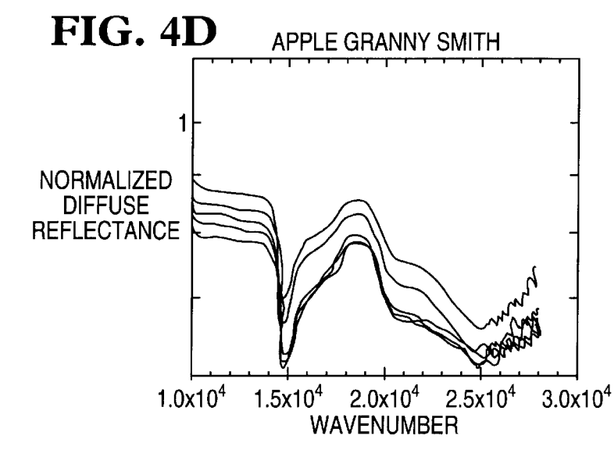
FIG. 4D shows a graph of a set of reference spectra for a granny smith apple.
Figure 4E:
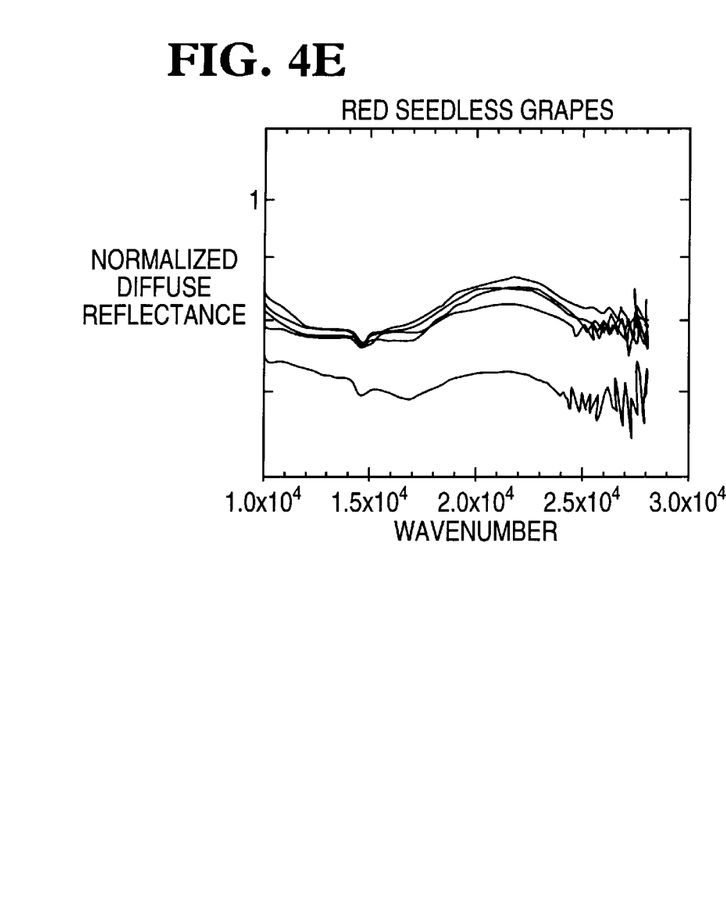
FIG. 4E shows a graph of a set of reference spectra for red seedless grapes.
Figure 4F:
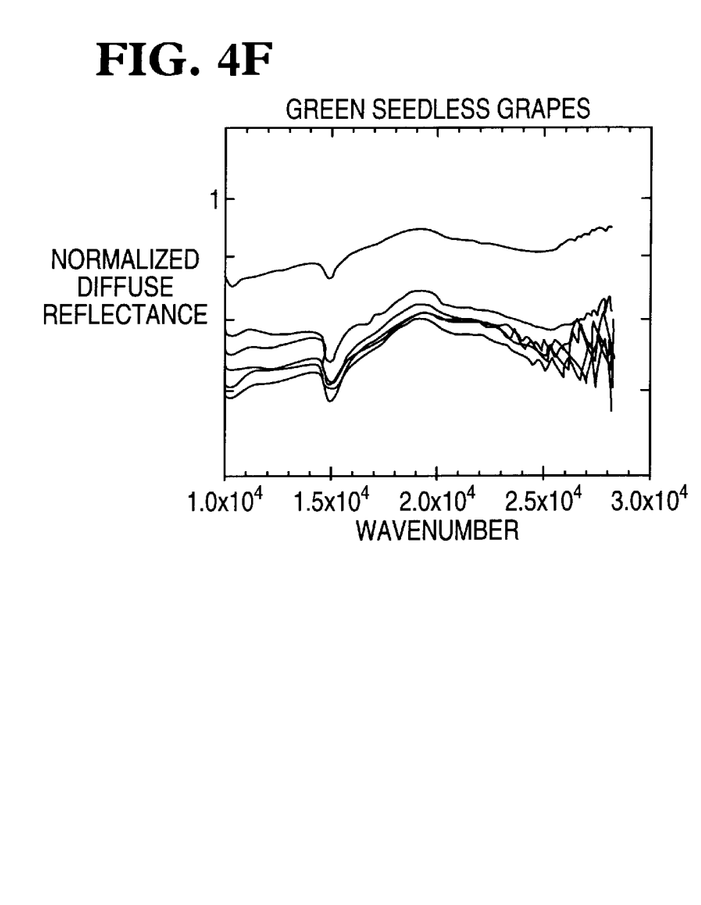
FIG. 4F shows a graph of a set of reference spectra for green seedless grapes.

Referring to FIG. 4A–4G, there are shown six different graphs of sets of reference spectra for common varieties of fruit sold in grocery stores. Each of the graphs illustrates a plot of diffuse reflectance as a function of wavenumber, wherein FIG. 4A is a set of reference spectra for a macintosh apple; FIG. 4B is a reference set for a Florida orange; FIG. 4C. is a reference set for a green pear; FIG. 4D is a reference set for a granny smith apple; FIG. 4E is a reference set for red seedless grapes; and FIG. 4F is a reference set for green seedless grapes. As can be seen, the sets of reference spectra are distinguishable from one another and essentially recognizable from their different spectral characteristics.

Once the matches have been computed, a display 60 (for example, a monitor or a display on the existing cash register) reads out a list of possible matches in rank order that have a probability of match greater than a predetermined threshold, for example, greater than 80% probability. An operator may check that the first listed item is correct and either accept the first choice or indicate the correct choice using the input device 62. As an alternative, the system could immediately accept the first choice, as in a fully automatic (unmanned) check-out system with a conveyor belt. As mentioned with respect to FIG. 1, in a preferred implementation of the system, the product to be identified would be sitting on a scale 22 and its weight would also be measured as part of the identification process. The scale 22 and optical identification system 10 are coupled to the computer (as is the bar code reader 20) in order to transfer electrical data for processing. As soon as the item identification 54 is made for the produce item in question, a total price for the identified item(s) can be computed by referencing the database, the weight and utilizing a previously stored price/unit figure. In a similar manner, then, to grocery items containing bar-code labels, the name and price of the produce item just identified would be printed on a grocery receipt using the item description, the weight, and the price per pound which was previously stored in the database. Accordingly, automatic recognition and price calculation is determined in an essentially single step process, similar to that of scanning a bar-coded item. Another advantage to the present invention optical recognition system is that the produce items need not be removed from the clear plastic produce bags in order to make an identification. This is because clear plastic does not significantly affect the reflectance from the produce if the light is gathered from a spot where the bag touches the produce and if known spectra of items in bags are stored in the reference data set. Also more than one item of a single produce-type may be identified and weighed at a single time. Additionally, the system can identify ripeness based on the characteristics of the test spectra of the item to be identified and a price can be assigned based on a degree of ripeness.

Although the present invention optical identification system has been described with respect to identifications of fresh produce, such as fruit, it will be understood that the system may also be implemented to identify any other item of commerce from which the optical reflectance can be measured. This method will be particularly valuable for items that are not economical to label with bar-codes. Examples of such articles include anything from lumber to loose clothing and fabrics and include meat, where the fat content can be measured as well. All that is necessary to accomplish the identification is a set of sufficiently distinct reference spectra with which a test spectrum can be readily compared.

From the above, it should be understood that the embodiments described, in regard to the drawings, are merely exemplary and that a person skilled in the art may make variations and modifications to the shown embodiments without departing from the spirit and scope of the invention. For example, the comparison software may be embodied in firmware together with relevant computing means as part an application specific integrated circuit (ASIC). All such variations and modifications are intended to be included within the scope of the invention as defined in the appended claims.

What is claimed is:

1. A produce recognition system comprising:

a checkout counter;

a bar code reader at the checkout counter, including a scale for producing a weight signal representing a weight of a produce item to be purchased during a transaction at the checkout counter;

a light source within the checkout counter for illuminating the produce item with light for identifying the produce item;

a spectrometer within the checkout counter which receives a reflected portion of the light from the produce item, including a dispersion element which disperses the reflected portion of the light into a plurality of finely spaced wavelengths of light, and a photodetector array which converts the plurality of finely spaced wavelengths of light to corresponding proportional electrical signals to produce a first spectra;

storage means for storing a set of reference spectra;

a computer coupled to the storage means, the bar code reader, and the spectrometer, which compares the first spectra from the photodetector array to the set of reference spectra to identify a second spectra within the set of reference spectra which most closely resembles the first spectra, and which determines a price of the produce item associated with the second spectra based upon the weight of the produce item.

2. The system as recited in claim 1, wherein the light source comprises a broad wavelength spectrum light source which emits light in a useful spectral range including part of the infrared spectral range, all of the visible spectral range, and part of the ultra-violet spectral range.

3. The system as recited in claim 1, wherein the light source comprises a tungsten-halogen lamp.

4. The system as recited in claim 1, wherein the photodetector array comprises a linear diode array.

5. The system as recited in claim 1, wherein the photodetector array comprises a charge-coupled device array.

6. The system as recited in claim 1, wherein the dispersion element resolves between 100 and 1100 individual wavelengths.

7. The system as recited in claim 1, wherein the computer is a transaction processing computer located at the checkout counter.

8. The system as recited in claim 1, wherein the computer displays a plurality of produce item identification choices including a choice associated with the second spectra and additional choices associated with additional spectra within the set of reference spectra, records entry of a single choice of the plurality of produce item identification choices by an operator, and adds a price associated with the single choice to the transaction.

9. The system as recited in claim 1, wherein the computer is located at the checkout counter.

10. The system as recited in claim 1, wherein the computer is located remotely from the checkout counter.

11. A produce recognition system comprising:

a checkout counter;

a bar code reader at the checkout counter, including a scale for producing a weight signal representing a weight of a produce item to be purchased during a transaction at the checkout counter;

a light source within the checkout counter for illuminating the produce item with light for identifying the produce item while the produce item is being weighed by the scale;

a spectrometer within the checkout counter which receives a reflected portion of the light from the produce item, including a dispersion element which disperses the reflected portion of the light into a plurality of finely spaced wavelengths of light, and a photodetector array which converts the plurality of finely spaced wavelengths of light to corresponding proportional electrical signals to produce a first spectra;

storage means for storing a set of reference spectra;

a computer coupled to the storage means, the bar code reader, and the spectrometer, which compares the first spectra from the photodetector array to the set of reference spectra to identify a second spectra within the set of reference spectra which most closely resembles the first spectra, and which determines a price of the produce item associated with the second spectra based upon the weight of the produce item.

* * * * *